(12) United States Patent
Sudhakar et al.

(10) Patent No.: US 7,326,795 B2
(45) Date of Patent: Feb. 5, 2008

(54) PROCESS AND INTERMEDIATES FOR THE PREPARATION OF (1R,2S,5S)-3-AZABI-CYCLO[3,1,0]HEXANE-2-CARBOXAMIDE, N-[3-AMINO-1-(CYCLOBUTYLMETHYL)-2,3-DIOXOPROPYL]-3-[(2S)-2-[[[1,1-DI-METHYLETHYL]AMINO]CARBONYL-AMINO]-3,3-DIMETHYL-1-OXOBUTYL]-6,6-DIMETHYL

(75) Inventors: Anantha Sudhakar, East Brunswick, NJ (US); Vilas Dahanukar, Hyderabad (IN); Ilia A. Zavialov, East Windsor, NJ (US); Cecilia Orr, Clark, NJ (US); Hoa N. Nguyen, Dayton, NJ (US); Juergen Weber, East Windsor, NJ (US); Ingyu Jeon, Fanwood, NJ (US); Minzhang Chen, Plainsboro, NJ (US); Michael D. Green, Willingboro, NJ (US); George S. Wong, Summit, NJ (US); Jeonghan Park, Whippany, NJ (US); Tetsuo Iwama, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 741 days.

(21) Appl. No.: 10/867,600

(22) Filed: Jun. 15, 2004

(65) Prior Publication Data

US 2005/0059800 A1  Mar. 17, 2005

Related U.S. Application Data

(60) Provisional application No. 60/479,517, filed on Jun. 17, 2003.

(51) Int. Cl.
*C07D 209/52* (2006.01)
*C07C 233/08* (2006.01)

(52) U.S. Cl. ...................... 548/515; 564/199

(58) Field of Classification Search ...................... None
See application file for complete search history.

(56) References Cited

U.S. PATENT DOCUMENTS 7,244,721 B2 * 7/2007 Saksena et al. ........ 514/210.21
2004/0254117 A9  12/2004 Saksena et al.

FOREIGN PATENT DOCUMENTS

WO  WO 02/08244  1/2002

OTHER PUBLICATIONS

International Search Report (PCT/US2004/018914)- 3pgs.
U.S. Appl. No. 10/052,386, filed Jan. 18, 2002.

* cited by examiner

*Primary Examiner*—Rebecca Anderson
*Assistant Examiner*—Michael P. Barker
(74) *Attorney, Agent, or Firm*—Patent Practioners of Schering Corporation

(57) ABSTRACT

In one embodiment, the present application relates to a process of making a compound of formula I:

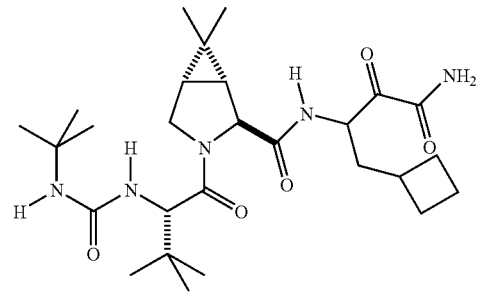

and to certain intermediate compounds that are made within the process of making the compound of formula I.

27 Claims, No Drawings

PROCESS AND INTERMEDIATES FOR THE PREPARATION OF (1R,2S,5S)-3-AZABI-CYCLO[3,1,0]HEXANE-2-CARBOXAMIDE, N-[3-AMINO-1-(CYCLOBUTYLMETHYL)-2,3-DIOXOPROPYL]-3-[(2S)-2-[[[1,1-DI-METHYLETHYL]AMINO]CARBONYL-AMINO]-3,3-DIMETHYL-1-OXOBUTYL]-6,6-DIMETHYL

PRIORITY APPLICATION

This patent application claims the benefit of priority from U.S. provisional application, Ser. No. 60/479,517 filed Jun. 17, 2003.

FIELD OF THE INVENTION

This invention relates to the process and intermediates for the preparation of (1R,2S,5S)-3-azabicyclo[3,1,0]hexane-2-carboxamide, N-[3-amino-1-(cyclobutylmethyl)-2,3-dioxopropyl]-3-[(2S)-2-[[[1,1-dimethylethyl]amino]carbonylamino]-3,3-dimethyl-1-oxobutyl]-6,6-dimethyl having the following structure of formula I:

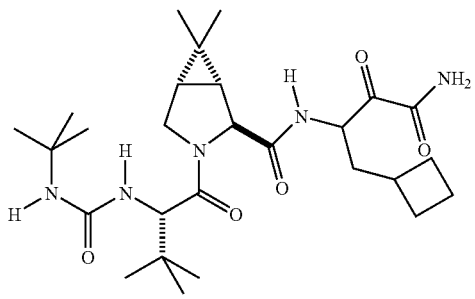

BACKGROUND OF THE INVENTION (1R, 2S, 5S)-3-Azabicyclo[3,1,0]hexane-2-carboxamide, N-[3-amino-1-(cyclobutylmethyl)-2,3-dioxopropyl]-3-[(2S)-2-[[[1,1-dimethylethyl]amino]carbonylamino]-3,3-dimethyl-1-oxobutyl]-6,6-dimethyl is disclosed in U.S. patent applications, Ser. No. 09/908,955 which was filed Jul. 19, 2001, and Ser. No. 10/052,386 which was filed Jan. 18, 2002, which are each incorporated herein by reference.

The compound of formula I is a hepatitis C virus ("HCV") protease inhibitor, useful for treating hepatitis C and related disorders. Specifically, the compound of formula I is an inhibitor of the HCV NS3/NS4a serine protease.

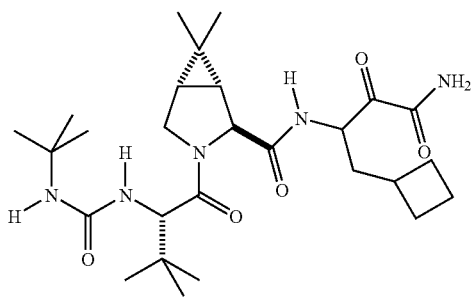

There remains a need for compounds useful in the treatment or prevention or amelioration of one or more symptoms of hepatitis C.

In view of the importance of hepatitis C virus ("HCV") protease inhibitors, new, novel methods of making such antagonists are always of interest.

SUMMARY OF THE INVENTION

In one embodiment, the present application relates to a process of making a compound of formula I:

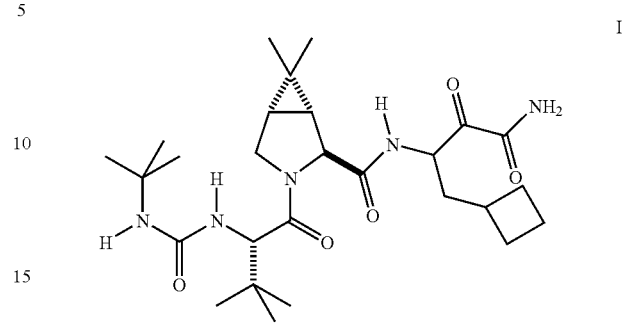

The invention also relates to certain intermediate compounds that are made within the process of making the compound of formula I.

The process of making the compound of formula I comprises:

(1) coupling a compound of formula II with a compound of formula III to yield a compound of formula IV:

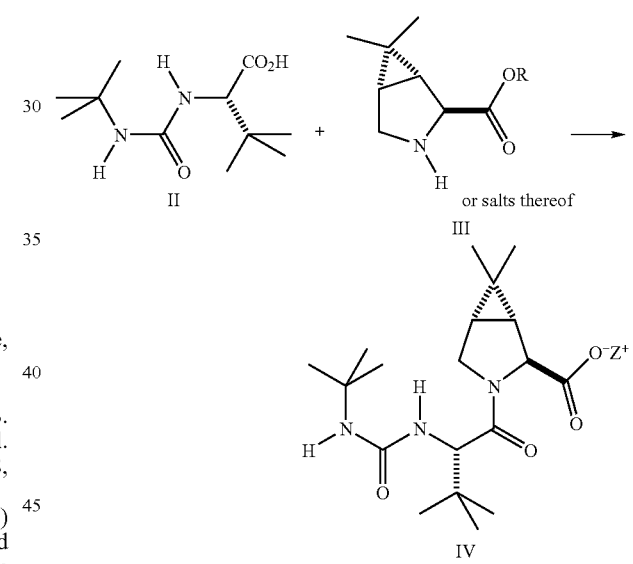

wherein $Z^+$ represents the cation of an amine or metal; and R is selected from the group consisting of alkyl, aryl and aralkyl;

(2) oxidizing the hydroxyl group of a compound of formula V to yield a compound of formula VI:

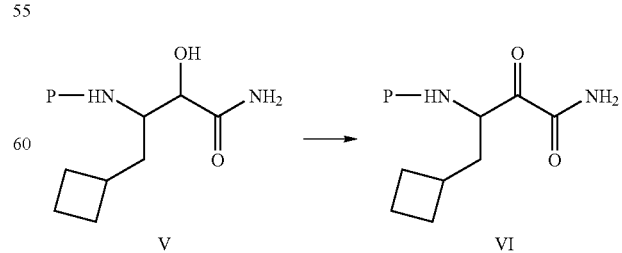

wherein P represents an N-protecting group;

(3) deprotecting the compound of formula VI to yield a compound of formula VII:

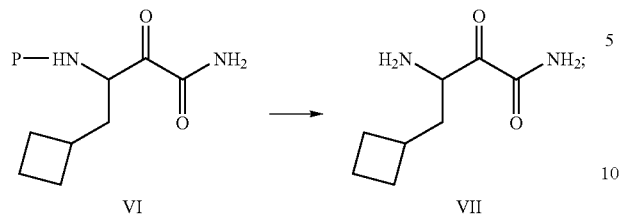

(4) generating a free acid compound of formula VII from the compound of formula IV:

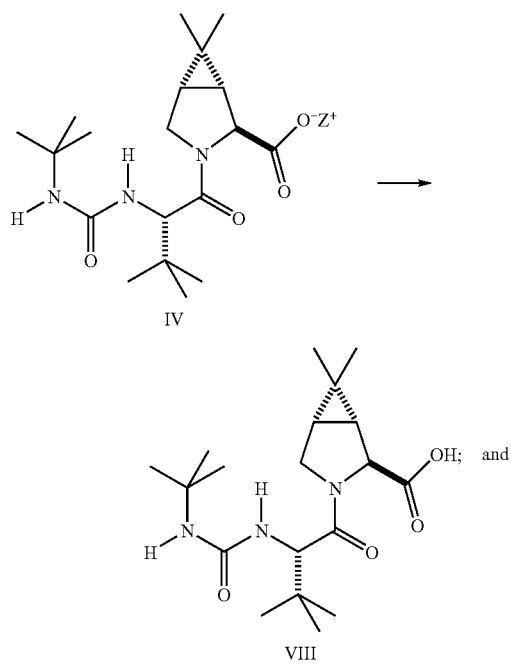

(5) coupling the compound of formula VII with a compound of formula VIII to yield the compound of formula I:

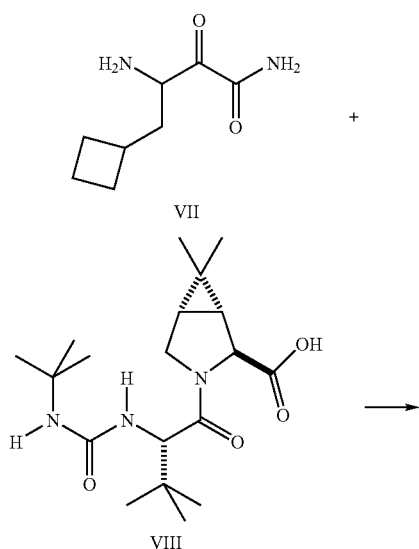

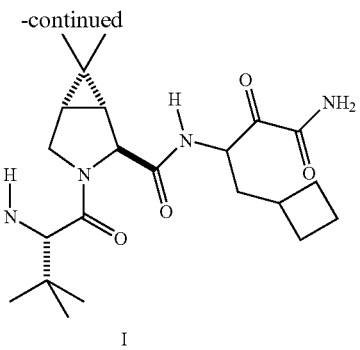

The inventive process to make the compound of formula I has several advantages: efficient resolution, purification and isolation of intermediate compounds, and a one step neutralization/coupling procedure to form the compound of formula I.

DESCRIPTION OF THE INVENTION

As used above, and throughout the specification, the following terms, unless otherwise indicated, shall be understood to have the following meanings:

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl, groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, and alkoxy. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N—$, $Y_1Y_2N$-alkyl-, $Y_1Y_2NC(O)—$ and $Y_1Y_2NSO_2—$, wherein $Y_1$ and $Y_2$ may be the same or different and are independently selected from the group consisting of hydrogen, alkyl, aryl, and aralkyl.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl groups is as previously described. Non-limiting examples of suitable aralkyloxy groups include benzyloxy and 1- or 2-naphthalenemethoxy. The bond to the parent moiety is through the ether oxygen.

"Alkylamino" means an —$NH_2$ or —$NH_3^+$ group in which one or more of the hydrogen atoms on the nitrogen is replaced by an alkyl group as defined above.

"Arylamino" means an —$NH_2$ or —$NH_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-$S(O_2)$— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Non-limiting examples of suitable solvates include ethanolates, methanolates, and the like. "Hydrate" is a solvate wherein the solvent molecule is $H_2O$.

In one embodiment, the present invention relates to a process for preparing the compound of formula I. The inventive process is schematically described in Scheme I below:

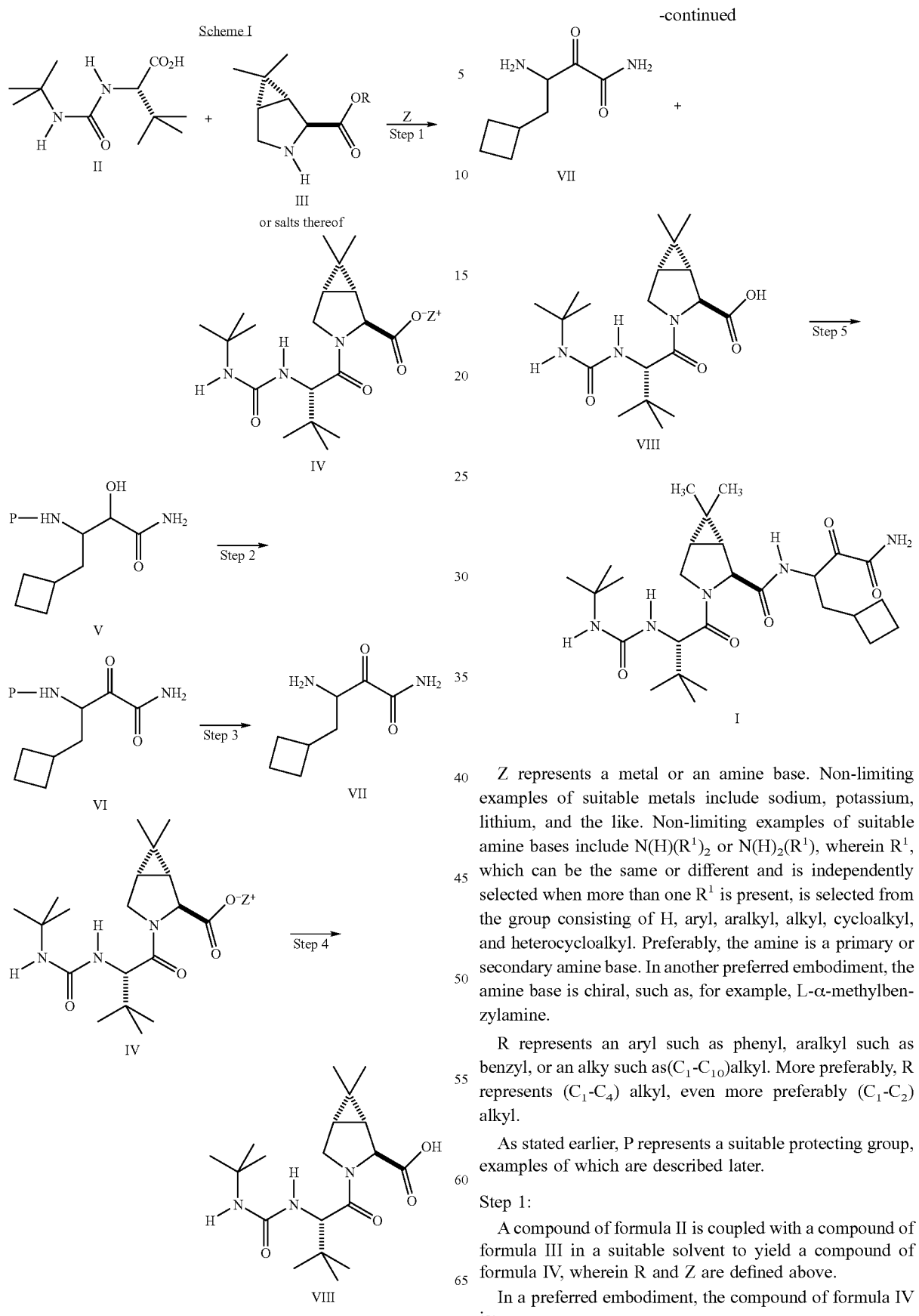

Z represents a metal or an amine base. Non-limiting examples of suitable metals include sodium, potassium, lithium, and the like. Non-limiting examples of suitable amine bases include $N(H)(R^1)_2$ or $N(H)_2(R^1)$, wherein $R^1$, which can be the same or different and is independently selected when more than one $R^1$ is present, is selected from the group consisting of H, aryl, aralkyl, alkyl, cycloalkyl, and heterocycloalkyl. Preferably, the amine is a primary or secondary amine base. In another preferred embodiment, the amine base is chiral, such as, for example, L-α-methylbenzylamine.

R represents an aryl such as phenyl, aralkyl such as benzyl, or an alky such as $(C_1-C_{10})$alkyl. More preferably, R represents $(C_1-C_4)$ alkyl, even more preferably $(C_1-C_2)$ alkyl.

As stated earlier, P represents a suitable protecting group, examples of which are described later.

Step 1:

A compound of formula II is coupled with a compound of formula III in a suitable solvent to yield a compound of formula IV, wherein R and Z are defined above.

In a preferred embodiment, the compound of formula IV is:

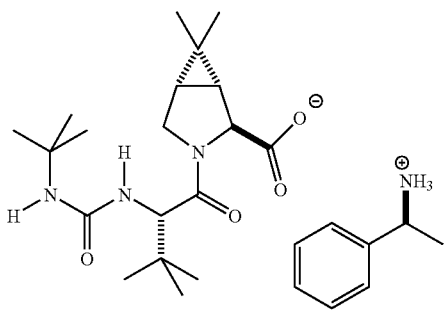

IV

In another preferred embodiment, the compound of formula III is a salt as shown below:

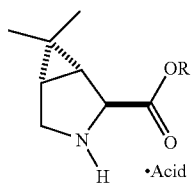

III wherein R is a $(C_1-C_4)$alkyl, and the acid can be any organic or inorganic acid, preferably inorganic acid such as $H_3PO_4$, $H_2SO_4$, HCl, or HBr. In another preferred embodiment, the compound of formula III is as shown below:

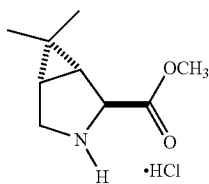

III

Standard peptide coupling procedures can be used such as the EDCI method or the isobutylchloroformate method, preferably the EDCI method. These peptide coupling procedures involve activation of the carboxylic acid group via mixed anhydride formation. The reaction in step 1 can be performed at a temperature ranging from about −20° C. to about 80° C., preferably from about 5° C. to about 50° C., more preferably from about 15° C. to about 25° C., for about 3-5 hours or until the reaction is complete. The molar ratio of the compound of formula II to the compound of formula III used in step 1 can vary widely, and is preferably about 1:1.

Non-limiting examples of reagents that can be used to activate the carboxylic acid include carbonic or carboxylic mixed anhydrides, N,N'-carbonyldiimidazole, ethyl chloroformate, 2-ethoxyl-ethoxycarbonyl-1,2-dihydroquinoline (EEDQ), ethyl chloroformate, isobutyl chloroformate, isopropenyl chloroformate, trimethylacetyl chloride, 2,4,6-trichlorobenzoyl chloride, isobutyl chloroformate, 4-nitrophenzl chloroformate, cyanuric chloride, oxalyl chloride, diethylaminosulfur trifluoride, bis (tetramethylene)fluoroformamidinium hexafluorophosphate (BPTFFH), Dimethylformamide/POCl$_3$ (Vilsmeier's reagent), phosphorus reagents, sulfur reagents, carbodiimides, pyridinium salts, phosphonium salts, uronium salts and the like.

Non-limiting examples of phosphorus reagents include diethyl chlorophosphate, diphenyl chlorophosphate, diethyl chlorophosphate, diphenyl phosphinic chloride, ethylene chlorophosphate, Lawesson's reagent and the like.

Non-limiting examples of sulfur reagents include thionyl chloride, methane sulfonyl chloride, p-toluenesulfonyl chloride, 4-chlorobenzenesulfonyl chloride, methanesulfonic anhydride and the like.

Non-limiting examples of carbodiimides include dicyclohexyldicarbodiimide (DCC), 1-(3-Diemthylaminpropyl)-3-ethylcarbodiimide hydrochloride (EDCI), diisopropyl carbodiimide and the like.

Non-limiting examples of pyridinium salts include 2-chloro-1-methylpyridinium iodide, 2-fluoro-1-methylpyridinium p-toluenesulfonate and the like.

Non-limiting examples of phosphonium salts include benzotriazole-1-yloxytris(dimethylaminophosphonium hexaflurophosphate (BOP), benzotriazole-1-yloxytris(pyrrolidino)-phosphonium hexaflurophosphate (PyBOP), bromotri(pyrrolidino)phosphonium hexafluorophsophate (PyBrOP)

Uronium salts: O-(1H-benzotriazole-1-yl)-N,N,N',N'-tetramethyluronium hexafluoroborate (HBTU), O-(1H-benzotriazole-1-yl)-N,N,N',N'-tetramethyluronium tetrafluoroborate (TBTU), O-(1,2-dihydro-2-oxo-1-pyridyl)-N,N,N',N'-tetramethyluronium tetrafluoroborate (TPTU), O-[(ethoxycarbonyl)cyanomethyleneamino]-N,N,N',N'-tetramethyluronium tetrafluoroborate (TOTU), 2-(5-norbornene-2,3-dicarboximido)-1,1,3,3-tetramethyluronium tetrafluoroborate (TNTU) and 2-succinimido-1,1,3,3-tetramethyluronium tetrafluoroborate (TSTU).

A preferred activating agent is EDCI. EDCI can be used generally in at least about 0.2 molar equivalents with respect to the compound of formula II, preferably at least about 0.8 molar equivalents with respect to the compound of formula II, more preferably from about 1.0 to about 1.4 molar equivalents with respect to the compound of formula II. Excess EDCI can be used.

In a preferred embodiment, the coupling reaction in step 1 includes adding a base to the reaction mixture. Non-limiting examples of bases that can be used include organic bases such as, for example, 2,4,6-collidine, 2,6-ditert-butyl-4-methylpyridine, 1-diethylamino-2-propanol, N-ethylamino-2-propanol, N-ethyldiisopropylamine, 4-ethylmorpholine, 1-ethylpiperidine, 2,6-lutidine, 4-methylmorpholine, 1-methylpiperidine, tribenzylamine, triethylamine, and the like, and inorganic bases. Non-limiting examples of suitable inorganic bases include metal hydroxides, metal alkoxides, metal bicarbonates, metal carbonates, such as MOH, MOR, MHCO$_3$, or M$_2$CO$_3$, wherein M represents Li, Na, K, Cs, Ba, Ca, Mg, and the like, and R represents an alkyl such as methyl, ethyl, propyl or isopropyl. Preferably, the base is 2,6-lutidine. The base can be used generally in at least about 0.2 molar equivalents with respect to the compound of formula III, preferably at least about 0.8 molar equivalents, more preferably from about 1.0 to about 1.4 molar equivalents. Excess base can be used.

In another embodiment, the coupling reaction in step 1 includes adding an additive to catalyze activation. Non-limiting examples of additives include 4-dimethylaminopyridine, 1-methylimidazole, 1,2,4-triazole, 4-(1-pyrrolidino) pyridine, N-hydroxysuccinimide, imidazole, 1-hydroxybenzotriazole (HOBt), etc. Preferably, the additive is 1-hydroxybenzotriazole.

Suitable solvents that can be used in step 1 include acetonitrile, dichloromethane, N,N-dimethylformamide, N,N-dimethylacetamide, dimethyl sulfoxide, 1,1,1,3,3,3-hexafluoro-2-propanol, 1-methyl-2-pyrrolidinone, tetrahydrofuran, trifluoroethanol, methyl tert-butyl ether, and the like, or mixtures thereof. In addition, mixtures of one or more of these solvents can be used with water if miscible. Preferably, the solvent is acetonitrile.

After the coupling reaction, an intermediate ester product which is formed is hydrolyzed to yield the free acid of the compound of formula IV. Preferably, the hydrolysis of the ester group is catalyzed by base or acid. Typical bases include MOH, MHCO$_3$, M$_2$CO$_3$ (where M=Li, Na, K, Cs, Ba, Ca, Mg, and the like), or MOR (where M is as defined above and R=methyl, ethyl, propyl, and isopropyl). Acidic conditions include mild sulfonic acids and the like.

The compound of formula IV formed in step 1 is isolated as a salt, preferably an (L)-α-methylbenzylamine salt. (L)-α-methylbenzylamine can be used generally in at least about 0.2 molar equivalents with respect to the free acid compound of formula IV, preferably at least about 0.8 molar equivalents, more preferably from about 1.0 to about 1.2 molar equivalents. Excess (L)-α-methylbenzylamine can be used.

Step 2:

A compound of formula V is oxidized in a suitable solvent to form a compound of formula VI. The preparation of compound V is disclosed in copending patent application CD06068US01 (based on provisional application Ser. No. 60/479487 filed on Jun. 17, 2003) filed on the same date herewith. Briefly, the preparation of compound V is represented in the Scheme below:

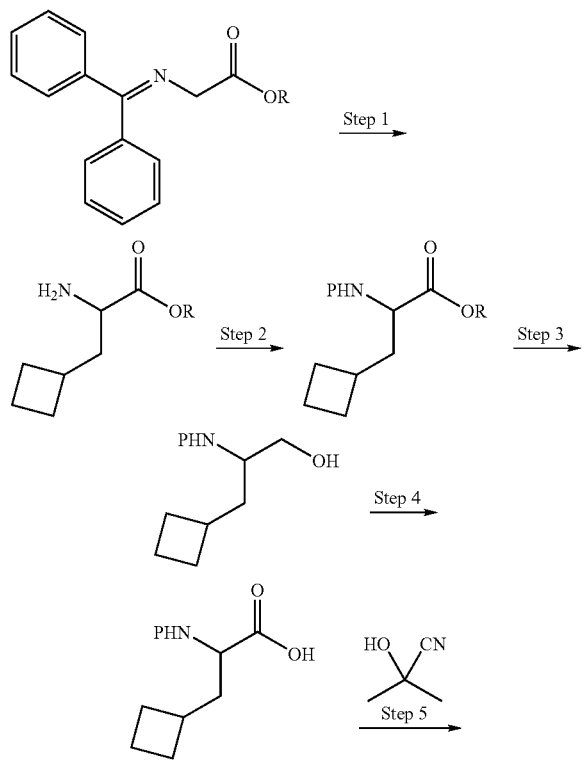

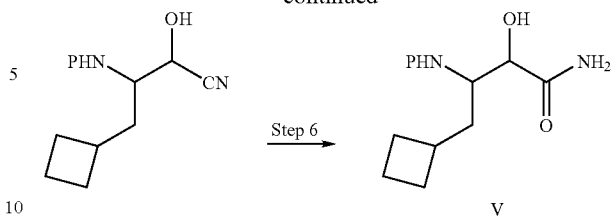

Examples of N-protecting groups (to introduce the P moiety) suitable in the practice of the invention include allyl, methoxymethyl, benzyloxymethyl, CY$_3$CO (where Y is a halogen), benzyloxycarbonyl, trityl, pivaloyloxymethyl, tetrahydranyl, benzyl, di(p-methoxyphenyl)methyl, triphenylmethyl, (p-methoxyphenyl)diphenylmethyl, diphenylphosphinyl, benzenesulfenyl, methylcarbamate, 2-trimethylsilylethyl carbamate, 1-methyl-1-phenylethyl carbamate, t-butyl carbamate ("t-Boc"), cyclobutyl carbamate, 1-methylcyclobutyl carbamate, adamantyl carbamate, vinyl carbamate, allyl carbamate, cinnamyl carbamate, 8-quinolyl carbamate, 4,5-diphenyl-3-oxazolin-2-one, benzyl carbamate, 9-anthrylmethyl carbamate, diphenylmethyl carbamate, S-benzylcarbamate, and the moiety:

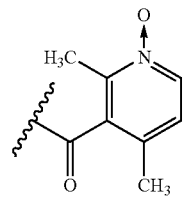

Preferred N-protecting groups include methylcarbamate, 2-trimethylsilylethyl carbamate, 1-methyl-1-phenylethyl carbamate, t-butyl carbamate ("t-Boc"), cyclobutyl carbamate, 1-methylcyclobutyl carbamate, adamantyl carbamate, vinyl carbamate, allyl carbamate, cinnamyl carbamate, 8-quinolyl carbamate, benzyl carbamate, 9-anthrylmethyl carbamate, diphenylmethyl carbamate, S-benzylcarbamate, more preferably t-Boc.

The oxidation can be carried out using DMSO based oxidation, KMnO$_4$, Br$_2$, MnO$_2$, ruthenium tetroxide/NaIO$_4$, pyridinium chlorochromate (PCC), pyridinium dichromate, sodium hypochlorite in acetic acid, BaBrO$_3$, or ceric ammonium nitrate. DMSO based oxidations are preferred.

DMSO oxidation preferably includes the combination of one or more of the following reagents with DMSO: oxalyl chloride with triethylamine, thionyl chloride with triethylamine, cyanuric chloride with triethylamine, DCC, EDCI, acetic anhydride, trifluoroacetic anhydride, SO$_3$-pyridine-triethylamine, p-toluenesulfonyl chloride, polyphosphoric acid, P$_2$O$_5$ and triethylamine, trichloromethyl chloroformate, methanesulfonic anhydride, and the like. Preferably, DMSO is used in combination with EDCI, and dichloroacetic acid as a solvent.

EDCI can be used generally in at least about 0.5 molar equivalents with respect to the compound of formula V, preferably at least about 1.0 molar equivalents with respect to the compound of formula V, more preferably from about 2.0 to about 3.0 molar equivalents with respect to the compound of formula V. Excess EDCI can be used. The reaction in step 2 can be carried out at a temperature ranging from about −25° C. to about 20° C., preferably from −15° C. to about −10° C., more preferably from about −10° C. to about 0° C.

Non-limiting examples of suitable solvents that can be used in step 2 include dichloroacetic acid in EtOAc, THF, acetonitrile, methylene chloride, isopropylacetate, methyl acetate, and the like, and mixtures thereof. Preferably, the solvent is dichloroacetic acid in EtOAc.

The compound of formula VI is preferably purified by crystallization.

Step 3:

The compound of formula VI from step 2 is deprotected to yield a compound of formula VII using an acid in a suitable solvent. The reaction in Step 2 can be carried out at a temperature ranging from about 0° C. to about 80° C., preferably from about 10° C. to about 50° C., more preferably from about 15° C. to about 30° C. Non-limiting examples of acids that can be used in Step 3 include inorganic acids, preferably $H_3PO_4$, $H_2SO_4$, HCl, and HBr, more preferably HCl. Non-limiting examples of suitable solvents include 2-isopropanol methanol, ethanol, acetonitrile, THF, toluene, EtOAc, iPrOAc, DMF, and NMP. The reaction in Step 3 can be carried out at a temperature ranging from about 20° C. to about 90° C., preferably from about 30° C. to about 60° C., more preferably from about 40° C. to about 50° C. for about 4 hours or until the reaction is complete. The compound of formula VII is preferably purified by crystallization.

Step 4:

The compound of formula IV is treated with an acid in a suitable solvent to yield the compound of formula VIII. Non-limiting examples of suitable acids include any organic or inorganic acids, preferably inorganic acids such as $H_3PO_4$, $H_2SO_4$, HCl, and HBr, more preferably HCl. Non-limiting examples of suitable solvents include water immiscible solvents, preferably EtOAc or MTBE, methylene chloride or isopropyl acetate, more preferably EtOAc or MTBE. The reaction in step 3 can be carried out at a temperature ranging from about −10° C. to about 80° C., preferably from about 0° C. to about 60° C., more preferably from about 25° C. to about 35° C. for about 1 hour or until the reaction is complete. Under preferred conditions, the compound of formula VIII is substantially optically pure (>99% de), and is utilized directly in the next step.

Step 5:

The compound of formula VII is coupled with the compound of formula VIII in a suitable solvent to yield a compound of formula I. The typical methods used in this peptide coupling are the same as discussed above in step 1. A preferred activation reagent is EDCI, a preferred additive is HOBt, a preferred base is N-methylmorpholine, and a preferred solvent is methyl tert-butyl ether (MTBE), all three preferably in a solvent such as, for example, acetonitrile. More preferably, the coupling step of step 5 is a mixed anhydride procedure with isobutylchloroformate as the activation reagent.

In a preferred embodiment, the compound of formula VII is generated in situ during coupling to avoid its buildup in solution. This could be achieved by charging either the compound of formula VII or a suitable amine base last to the batch already containing all other reagents and regulating the addition rate to achieve optimal reaction performance.

In another preferred embodiment, the compound of formula I is purified through the formation of a bisulfite adduct having the following formula:

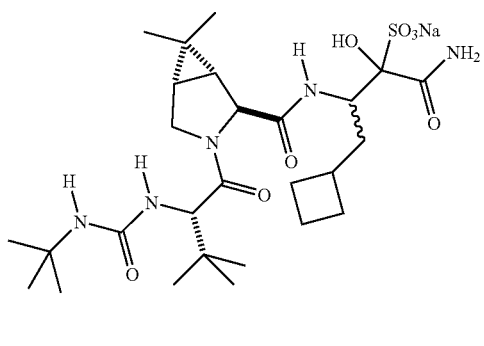

Methods of purification using bisulfite adducts are described in *Advanced Organic Chemistry*, 4th Edition, *Jerry March*, John Wiley and Sons, 1992.

The following non-limiting EXAMPLES are provided in order to further illustrate the present invention. It will be apparent to those skilled in the art that many modifications, variations and alterations to the present disclosure, both to materials, methods and reaction conditions, may be practiced. All such modifications, variations and alterations are intended to be within the spirit and scope of the present invention.

EXAMPLES

Unless otherwise stated, the following abbreviations have the stated meanings in the Examples below:

MHz=Megahertz

NMR=nuclear magnetic resonance spectroscopy

DMSO=dimethylsulfoxide

EDCI=1-(3-Diemthylaminpropyl)-3-ethylcarbodiimide hydrochloride

MTBE=methyl tert-butyl ether

NMM=N-methylmorpholine

Equiv=equivalent(s)

IPA=isopropyl alcohol

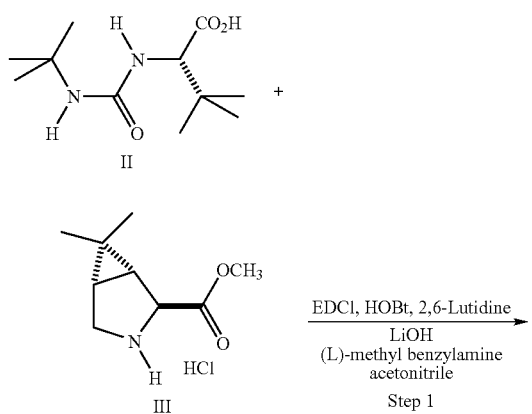

Scheme I

-continued

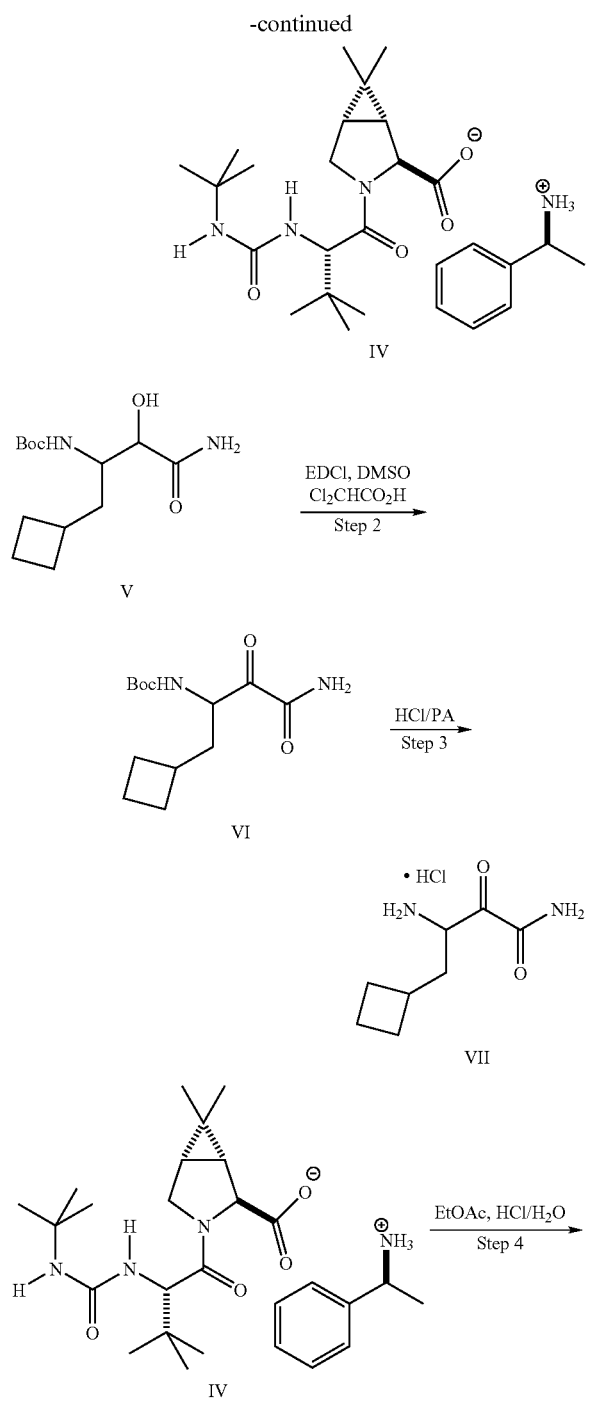

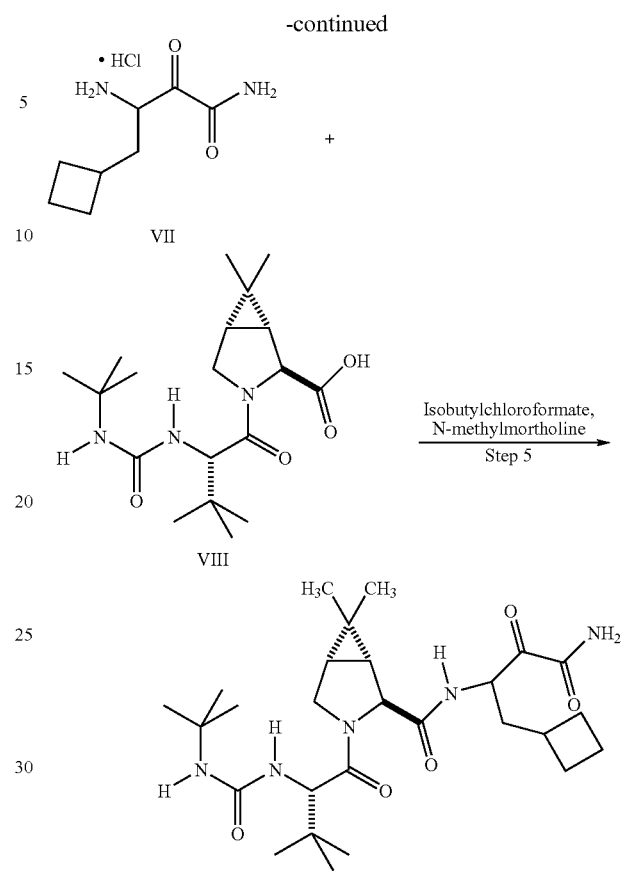

Experimental Procedure

Step 1:

1.0 equivalent of the compound of formula II was charged to vessel A, followed by 3 volumes of acetonitrile and 2.25 eq of 2,6-lutidine while the temperature was maintained between 20° C. and 30° C. Then 1.0 eq of the compound of formula III, 0.5 eq of 1-hydroxybezotriazole hydrate, 1.2 eq of EDCI hydrochloride and 4 volumes of acetonitrile were charged to vessel B between 10° C. and 20° C. The solution containing the compound of formula II was then immediately added to the slurry containing the compound of formula III. The reaction was complete in about 3 to 5 hours.

The reaction mixture was then diluted with 6 volumes of MTBE and the pH was adjusted with 3N hydrochloric acid, extracted, washed with sodium bicarbonate solution and concentrated. After addition of 6× of acetonitrile and reconcentration to about 7 volumes of a 10% aqueous lithium hydroxide solution (2 equiv) were charged. The batch was agitated for 3 hours between 20° C. and 25° C. Dilution of the batch with 4 volumes of isopropyl acetate was followed by pH adjustment with 3N hydrochloric acid, extraction and sodium chloride wash. Concentration with additional isopropyl acetate prepared the batch for the salt formation step. L(−)-α-methylbenzylamine (1.1 equiv) was charged to the free acid solution (6 to 6.5 volumes) at 70° C. to 80° C. The temperature was maintained for about 30 minutes and then the batch was cooled to 20° C. to 25° C. The salt product was filtered and washed with 3 volumes of i-propyl acetate. The wet cake was dried under vacuum at 40° C. to 50° C. for 3 hours and then at 75° C. to 85° C. for at least 10 hours to provide the compound of formula IV in about 85-95% molar yield.

$^1$H-NMR (400 MHz, CD$_3$OD): δ 7.45 (m, 5H), 4.92 (s, broad, 5H), 4.39 (q, 3H), 4.33 (dd, 1H), 4.28 (s, 1H), 4.03 (d, 1H), 3.96 (dd, 1H), 1.63 (d, 3H), 1.45 (m, 2H), 1.28 (s, 9H), .1.05 (s, 3H), 1.04 (s, 9H), 0.91 (s, 3H); $^{13}$C-NMR (100.6 MHz, CD$_3$OD): δ179.3, 173.3, 160.1, 140.7, 130.6, 130.4, 128.0, 63.9, 59.2, 52.6, 51.1, 49.3, 36.4, 33.3, 30.1, 28.8, 27.5, 27.2, 21.5, 20.5, 13.6.

Step 2:

To a stirred mixture of 1 equiv of the compound of formula V was charged 4 volumes of isopropanol and 2.5 equiv of EDCI in 6 volumes of ethyl acetate was added 2 volumes of methyl sulfoxide. The mixture was then cooled to −5° C. To this cooled mixture was slowly added about 1.5 equiv of dichloroacetic acid over about 1 hour. After addition, the mixture was stirred at −5° C. for about 21 hours and water (5 volumes) was added. The mixture was then warmed to 20° C. After separation, the aqueous layer was extracted with ethyl acetate (3 volumes). The combined organic layers were washed with water (5 volumes). Ethyl acetate in the organic layer was displaced with heptane via distillation. After solvent displacement, the mixture was stirred at 20° C. for 2 hours and filtered. The wet cake was washed with heptane (2 portions of 2.5 volumes) and dried under vacuum at 40° C. for 12 hours to give 70% molar yield of the compound of formula VI.

$^1$H NMR (DMSO): δ 8.00 (s, 1 H), 7.72 (s, 1 H), 7.20-7.08 (m, 1 H), 4.75-4.62 (m, 1H), 3.35 (s, 1H), 2.48-2.30 (m, 1H), 2.10-1.48 (m, 8 H), 1.41-1.22 (m, 9 H).

Step 3:

To a stirred mixture of 1 equivalent of the compound of formula VI and 6 volumes of isopropyl alcohol, 2 volumes of 5-6N HCl in isopropanol was added to the mixture. The batch was heated to 40-50° C. for about 4 hours and sampled for reaction completion. The mixture was concentrated to about 2 volumes and cooled to 25-35° C. Then 10 volumes of methyl tert-butylether was charged and the batch was cooled to 0-5° C. After one hour the precipitated solids were filtered and washed with more methyl tert-butyl ether. The wet product was dried under vacuum at 40° C. for 12 hours to give 91% molar yield of the compound of formula VII.

$^1$H NMR (DMSO): δ 8.55 (s, 3 H), 8.32 (s, 1 H), 8.06 (s, 1 H), 4.55-4.62 (m 1 H), 2.21-1.44 (m, 9 H).

Step 4:

A solution of 1N HCl in water (2.5 volumes) was charged to 1 equivalent of the compound of formula IV in methyl tert-butyl ether (4 volumes, MTBE) and then stirred at 20-25° C. for 1 hour. The organic layer was separated and the aqueous layer was extracted with MTBE (2 volumes). The combined organic layer was dried, evaporated to get a solid or used as is for the next step (or solvent MTBE is replaced with acetonitrile or EtOAc by distillation and then used in the next step).

EDCI Method:

To a solution of the compound of formula VIII (1 equiv, obtained above) in acetonitrile (10 volumes) were added the compound of formula VII (1.3 equiv) and, EDCI (1.5 equiv) and 1-hydroxybenzotriazole (0.3 equiv). The suspension was stirred and then N-methylmorpholine (1.1 equiv) was added over a period of 1 hour at 15-20° C. The reaction mixture was concentrated under vacuum to about 3 volumes and then diluted with MTBE (4 volumes) and 1N HCl (4 volumes). The mixture was stirred and the organic layer was separated and treated with 5% aqueous NaHCO$_3$ solution (2 portions of 3 volumes). The organic layer was concentrated to provide the compound of formula I in about 85-90% molar yield.

$^1$H NMR (500 MHz, DMSO-d$_6$) δ 8.20-8.30 (dd, 1H), 7.76-8.04 (broad, 2H), 5.97 (s, 1H), 5.86 (dd, 1H), 4.85 (m, 1H), 4.26 (s, 1H), 4.11 (d, 1H), 3.74-3.96 (m, 2H), 2.40 (m, 1H), 1.80 (m, 4H), 1.73 (m, 2H), 1.60-1.70 (m, 2H), 1.43 (m, 1H), 1.26 (dd, 1H), 1.17 (s, 9H), 0.82-1.00 (m, 6H), 0.89 (m, 9H).

$^{13}$C NMR (75 MHz, DMSO-d$_6$) δ 197.9, 197.2, 174.4, 173.7, 171.6, 171.5, 171.1, 171.0, 170.8, 163.1, 162.8, 157.5, 157.4, 157.3, 157.2, 94.4, 94.3, 60.8, 59.8, 59.4, 59.2, 56.9, 56.8, 53.7, 52.3, 52.1, 51.8, 49.0, 48.9, 48.8, 47.5, 40.1, 40.0, 39.5, 39.2, 39.0, 36.8, 36.6, 35.8, 35.7, 34.2, 34.1, 34.0, 32.4, 32.2, 32.1, 31.9, 30.7, 30.6, 30.4, 29.4, 29.1, 28.0, 27.9, 27.8, 27.7, 27.4, 27.2, 27.1, 26.9, 26.4, 26.2, 26.1, 26.0, 18.7, 18.6, 18.5, 18.4, 18.0, 17.9, 17.8, 17.7, 12.6, 12.5.

Isobutylchloroformate Method:

To a solution of the compound formula VIII (1 equiv, obtained above) in ethyl acetate (10 volumes) were added the compound of formula VII (1.2 equiv) and isobutylchloroformate (1.5 equiv). The suspension was cooled to 0-10° C. and then N-methylmorpholine (1.1 equiv, NMM) was added over a period of 1 hour. The reaction mixture was diluted with MTBE (5 volumes) 20 and then the precipitated NMM. HCl salt was filtered. The filtrate was washed with 1N HCl (2 volumes) and then organic layer was washed with 5% aqueous NaHCO$_3$ solution (3 volumes). The organic layer was concentrated to provide the compound of formula I in about 90-95% molar yield.

$^1$H NMR (500 MHz, DMSO-d$_6$) δ 8.20-8.30 (dd, 1H), 7.76-8.04 (broad, 2H), 5.97 (s, 1H), 5.86 (dd, 1H), 4.85 (m, 1H), 4.26 (s, 1H), 4.11 (d, 1H), 3.74-3.96 (m, 2H), 2.40 (m, 1H), 1.80 (m, 4H), 1.73 (m, 2H), 1.60-1.70 (m, 2H), 1.43 (m, 1H), 1.26 (dd, 1H), 1.17 (s, 9H), 0.82-1.00 (m, 6H), 0.89 (m, 9H).

$^{13}$C NMR (75 MHz, DMSO-d$_6$) δ 197.9, 197.2, 174.4, 173.7, 171.6, 171.5, 171.1, 171.0, 170.8, 163.1, 162.8, 157.5, 157.4, 157.3, 157.2, 94.4, 94.3, 60.8, 59.8, 59.4, 59.2, 56.9, 56.8, 53.7, 52.3, 52.1, 51.8, 49.0, 48.9, 48.8, 47.5, 40.1, 40.0, 39.5, 39.2, 39.0, 36.8, 36.6, 35.8, 35.7, 34.2, 34.1, 34.0, 32.4, 32.2, 32.1, 31.9, 30.7, 30.6, 30.4, 29.4, 29.1, 28.0, 27.9, 27.8, 27.7, 27.4, 27.2, 27.1, 26.9, 26.4, 26.2, 26.1, 26.0, 18.7, 18.6, 18.5, 18.4, 18.0, 17.9, 17.8, 17.7, 12.6, 12.5.

It will be understood that various modifications can be made to the embodiments and examples disclosed herein. Therefore, the above description should not be construed as limiting, but merely as exemplifications of preferred embodiments. Those skilled in the art will envision various modifications within the scope and spirit of the claims appended hereto.

What is claimed is:

1. A process of making the compound of formula I comprising:

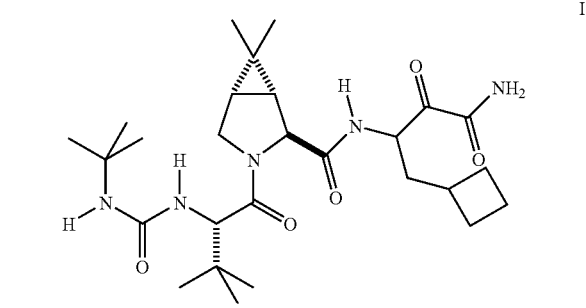

(1) coupling a compound of formula II with a compound of formula III to yield a compound of formula IV:

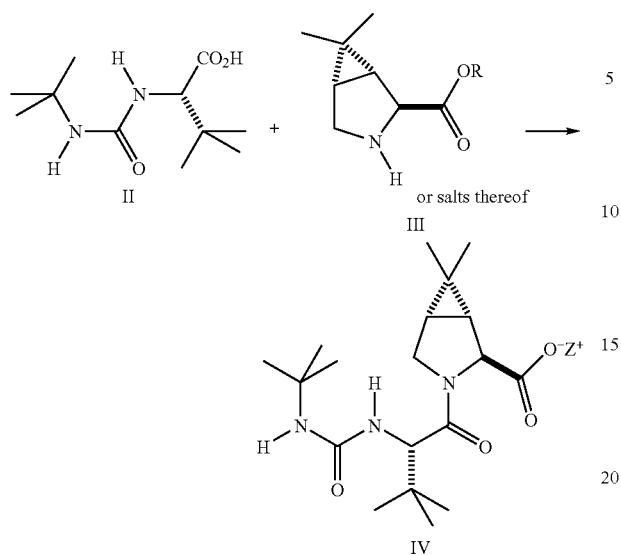

wherein $Z^+$ represents the cation of an amine or metal; and R is selected from the group consisting of alkyl, aryl and aralkyl;

(2) oxidizing the hydroxyl group of a compound of formula V to yield a compound of formula VI:

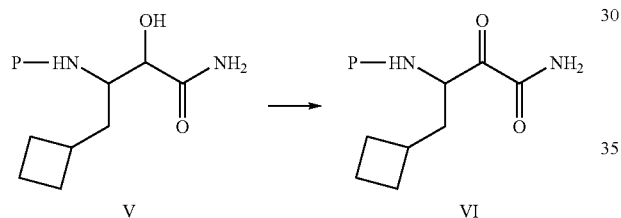

wherein P represents an N-protecting group;

(3) deprotecting the compound of formula VI to yield a compound of formula VII:

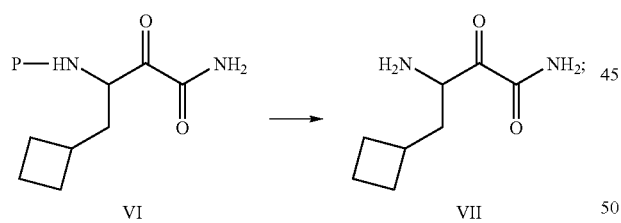

(4) generating a free acid compound of formula VIII from the compound of formula IV:

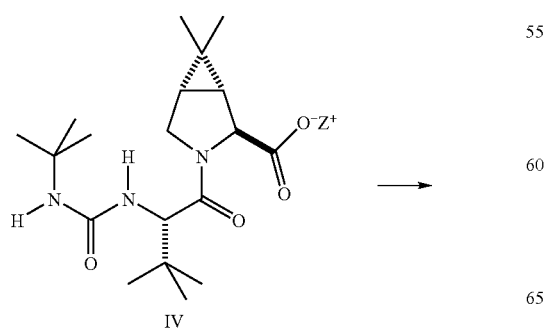

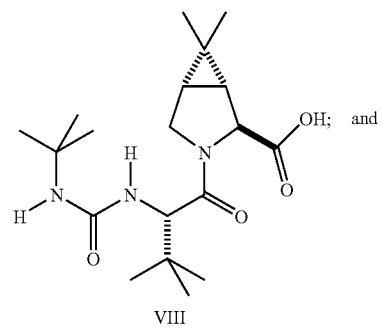

(5) coupling the compound of formula VII with a compound of formula VIII to yield the compound of formula I:

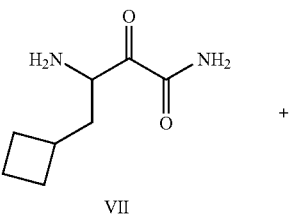

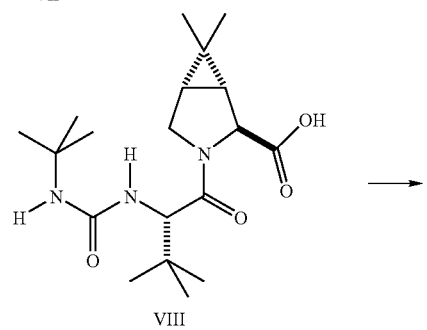

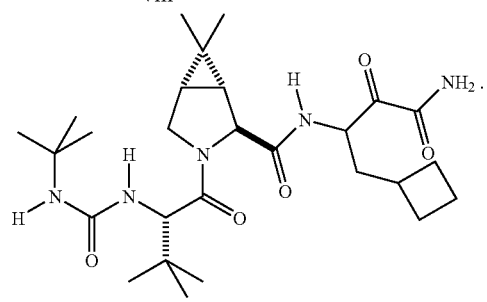

2. The process according to claim 1 wherein $Z^+$ represents a primary or secondary amine base.

3. The process according to claim 2, said primary or secondary amine base is $N(H)(R)_2$ or $N(H)_2(R)$, wherein R, which can be the same or different and is independently selected when more than one R is present, is selected from the group consisting of H, aryl, aralkyl, alkyl, cycloalkyl, and heterocycloalkyl.

4. The process according to claim 1 wherein the compound of formula IV is:

IV

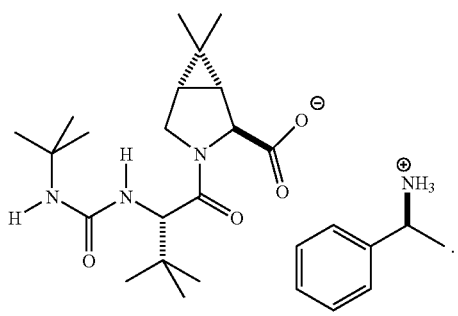

5. The process according to claim 1, wherein the coupling of step 1 comprises activating the carboxylic acid group of the compound of formula II with an activation agent selected from the group consisting of carbonic or carboxylic mixed anhydrides, N,N'-carbonyldiimidazole, ethyl chloroformate, 2-ethoxyl-ethoxycarbonyl-1,2-dihydroquinoline (EEDQ), ethyl chloroformate, isobutyl chloroformate, isopropenyl chloroformate, trimethylacetyl chloride, 2,4,6-trichlorobenzoyl chloride, isobutyl chloroformate, 4-nitrophenzl chloroformate, cyanuric chloride, oxalyl chloride, diethylaminosulfur trifluoride, bis (tetramethylene)fluoroformamidinium hexaflurorophosphate (BPTFFH), Dimethylformamide/POCI₃ (Vilsmeier's reagent), phosphorus reagents, sulfur reagents, carbodiimides, pyridinium salts, and phosphonium salts.

6. The process according to claim 5, wherein said activating agent is a carbodiimide selected from the group consisting of dicyclohexyldicarbodiimide (DCC), 1-(3-Diemthylaminpropyl)-3-ethylcarbodiimide hydrochloride (EDCI), and diisopropyl carbodiimide.

7. The process according to claim 6, wherein said carbodiimide is EDCI.

8. The process according to claim 1, wherein step 1 further comprises adding a base selected from the group consisting of 2,4,6-collidine, 2,6-ditert-butyl-4-methylpyridine, 1-diethylamino-2-propanol, N-ethylamino-2-propanol, N-ethyldiisopropylamine, 4-ethylmorpholine, 1-ethylpiperidine, 2,6-lutidine, 4-methylmorpholine, 1-methylpiperidine, tribenzylamine, triethylamine, metal hydroxide, metal alkoxide, metal bicarbonate, and metal carbonate.

9. The process according to claim 8, wherein said base is 2,6-lutidine.

10. The process according to claim 1, wherein step 1 further comprises adding an additive selected from the group consisting of 4-dimethylaminopyridine, 1-methylmimidazole, 1,2,4-triazole, 4-(1-pyrrolidino)pyridine, N-hydroxysuccinimide, imidazole, and 1-hydroxybenzotriazole.

11. The process according to claim 10, wherein said additive is 1-hydroxybenzotriazole.

12. The process according to claim 1, wherein the compound of formula III is used in the form of a salt of formula:

III

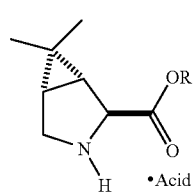

wherein R represents (C₁-C₄) alkyl and the acid is selected from the group consisting of H₃PO₄, H₂SO₄, HCl, or HBr.

13. The process according to claim 12, wherein R is methyl, and said acid is HCl.

14. The process according to claim 1, wherein an acid is added to catalyze the formation of the compound of formula IV.

15. The process according to claim 1, wherein the N-protecting group of the compounds of formula V and VI in step 2 is selected from the group consisting of allyl, methoxymethyl, benzyloxymethyl, CY₃CO, wherein each Y can be the same or different and is independently selected from the group consisting of halogen, benzyloxycarbonyl, trityl, pivaloyloxymethyl, tetrahydranyl, benzyl, di(p-methoxyphenyl)methyl, triphenylmethyl, (p-methoxyphenyl)diphenylmethyl, diphenylphosphinyl, benzenesulfenyl, methylcarbamate, 2-trimethylsilylethyl carbamate, 1-methyl-1-phenylethyl carbamate, t-butyl carbamate ("t-Boc"), cyclobutyl carbamate, 1-methylcyclobutyl carbamate, adamantyl carbamate, vinyl carbamate, allyl carbamate, cinnamyl carbamate, 8-quinolyl carbamate, 4,5-diphenyl-3-oxazolin-2-one, benzyl carbamate, 9-anthrylmethyl carbamate, diphenylmethyl carbamate, S-benzylcarbamate, and the moiety:

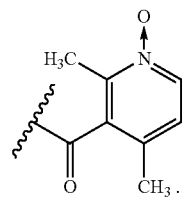

16. The process according to claim 1, wherein the oxidation method in step 2 is catalyzed by an oxidizing agent selected from the group consisting of DMSO based oxidation, KMnO₄, Br₂, MnO₂, ruthenium tetroxide/NaIO₄, pyridinium chlorochromate (PCC), pyridinium dichromate, sodium hypochlorite in acetic acid, BaBrO₃, and ceric ammonium nitrate.

17. The process according to claim 16, wherein the oxidation in step 2 is DMSO based oxidation.

18. The process according to claim 1, wherein the compound of formula VI in step 2 is purified by crystallization.

19. The process according to claim 1, wherein the compound of formula VI in step 3 is deprotected with an acid selected from the group consisting of H₃PO₄, H₂SO₄, HCl, and HBr.

20. The process according to claim 1, wherein the compound of formula VII in step 3 is purified by crystallization.

21. The process according to claim 1, wherein the compound of formula IV in step 4 is treated with an acid selected from the group consisting of H₃PO₄, H₂SO₄, HCl, and HBr.

22. The process according to claim 1, wherein the coupling in step 5 is a mixed anhydride procedure with isobutylchloroformate.

23. The process according to claim 1, wherein the compound of formula VII in step 5 is generated in situ during coupling.

24. A compound of the formula:
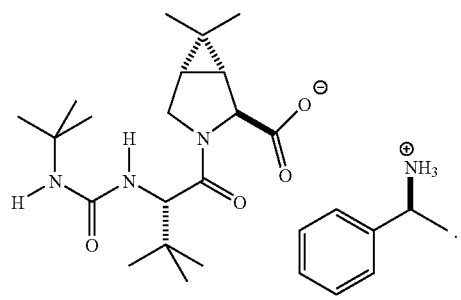
IV
25. A compound of the formula:
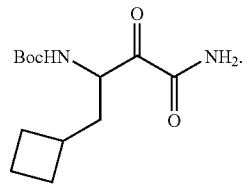
VI
26. A compound of the formula:
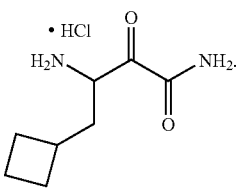
V
27. A compound of the formula:
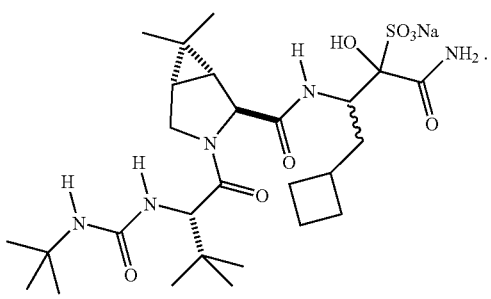
VII
* * * * *